(12) United States Patent
Williams

(10) Patent No.: US 6,746,685 B2
(45) Date of Patent: Jun. 8, 2004

(54) BIOABSORBABLE, BIOCOMPATIBLE POLYMERS FOR TISSUE ENGINEERING

(75) Inventor: Simon F. Williams, Sherborn, MA (US)

(73) Assignee: Tepha, Inc., Cambridge, MA (US)

(*) Notice: Subject to any disclaimer, the term of this patent is extended or adjusted under 35 U.S.C. 154(b) by 0 days.

(21) Appl. No.: 10/289,479

(22) Filed: Nov. 6, 2002

(65) Prior Publication Data

US 2003/0072784 A1 Apr. 17, 2003

Related U.S. Application Data

(62) Division of application No. 09/518,123, filed on Mar. 3, 2000, now Pat. No. 6,514,515.
(60) Provisional application No. 60/122,827, filed on Mar. 4, 1999.

(51) Int. Cl.⁷ ............................... A61F 2/02; A61K 9/50
(52) U.S. Cl. ........................ 424/424; 424/425; 424/501; 424/502
(58) Field of Search ................................ 424/424, 425, 424/501, 502

(56) References Cited

U.S. PATENT DOCUMENTS

| | | |
|---|---|---|
| 3,982,543 A | 9/1976 | Schmitt et al. |
| 4,711,241 A | 12/1987 | Lehmann |
| 4,826,493 A | 5/1989 | Martini et al. |
| 4,880,592 A | 11/1989 | Martini et al. |
| 4,910,145 A | 3/1990 | Holmes et al. |
| 5,245,023 A | 9/1993 | Peoples et al. |
| 5,271,961 A | 12/1993 | Mathiowitz et al. |
| 5,292,860 A | 3/1994 | Shiotani et al. |
| 5,334,698 A | 8/1994 | Witholt et al. |
| 5,468,253 A | 11/1995 | Bezwada et al. |
| 5,480,794 A | 1/1996 | Peoples et al. |
| 5,489,470 A | 2/1996 | Noda |
| 5,502,116 A | 3/1996 | Noda |
| 5,502,158 A | 3/1996 | Sinclair et al. |
| 5,512,669 A | 4/1996 | Peoples et al. |
| 5,516,883 A | 5/1996 | Hori et al. |
| 5,536,564 A | 7/1996 | Noda |
| 5,550,173 A | 8/1996 | Hammond et al. |
| 5,563,239 A | 10/1996 | Hubbs et al. |
| 5,705,187 A | 1/1998 | Unger |
| 5,711,933 A | 1/1998 | Bichon et al. |
| 5,789,536 A | 8/1998 | Liggat et al. |
| 6,245,537 B1 | 6/2001 | Williams et al. |
| 6,454,811 B1 * | 9/2002 | Sherwood et al. ....... 623/23.76 |

FOREIGN PATENT DOCUMENTS

| | | |
|---|---|---|
| DE | 39 37 649 A1 | 5/1991 |
| EP | 0 258 781 A1 | 3/1988 |
| EP | 0 423 484 A1 | 4/1991 |
| EP | 0 601 885 A1 | 6/1994 |
| EP | 0 628 586 A1 | 12/1994 |

(List continued on next page.)

OTHER PUBLICATIONS

Agostini, et al., "Synthesis and Characterization of Poly–β–Hydroxybutyrate. I. Synthesis of Crystalline DL Poly–β–Hydroxybutyrate from DL–β–Butyrolactone," *Polym. Sci.*, Part A–1 9:2775–87 (1971).

(List continued on next page.)

*Primary Examiner*—Carlos A. Azpuru
(74) *Attorney, Agent, or Firm*—Holland & Knight LLP

(57) ABSTRACT

Bioabsorbable biocompatible polymers which provide a good match between their properties and those of certain tissue structures are provided. The bioabsorbable biocompatible polymers can be prepared with tensile strengths, elongation to breaks, and/or tensile modulus (Young's modulus) values of the tissues of the cardiovascular, gastrointestinal, kidney and genitourinary, musculoskeletal, and nervous systems, as well as those of the oral, dental, periodontal, and skin tissues. Methods for processing the bioabsorbable biocompatible polymers into tissue engineering devices are also provided.

6 Claims, 2 Drawing Sheets

FOREIGN PATENT DOCUMENTS

| | | |
|---|---|---|
| EP | 0 754 467 A1 | 1/1997 |
| JP | 4-326932 A | 11/1992 |
| JP | 5-023189 A | 2/1993 |
| JP | 7-275344 A | 10/1995 |
| WO | WO 92/18164 A1 | 10/1992 |
| WO | WO 93/20134 A1 | 10/1993 |
| WO | WO 94/06886 A1 | 3/1994 |
| WO | WO 95/03356 A1 | 2/1995 |
| WO | WO 95/20614 A1 | 8/1995 |
| WO | WO 95/20615 A1 | 8/1995 |
| WO | WO 95/20621 A1 | 8/1995 |
| WO | WO 95/23250 A1 | 8/1995 |
| WO | WO 95/33874 A1 | 12/1995 |
| WO | WO 96/00263 A1 | 1/1996 |
| WO | WO 96/08535 A1 | 3/1996 |
| WO | WO 96/18420 A1 | 6/1996 |
| WO | WO 98/04292 A1 | 2/1998 |
| WO | WO 98/39453 A1 | 9/1998 |
| WO | WO 98/51812 A2 | 11/1998 |
| WO | WO 99/32536 A1 | 7/1999 |

OTHER PUBLICATIONS

Akhtar, "Physiomechanical Properties of bacterial P(HB–HV) Polyesters and Their Uses in drug Delivery," The British Library Document Supply Centre, UMI, (1990).

Anderson, et al., "Occurence, Metabolism, metabolic Role, and Industrial Uses of bacterial Polyhydroxyalkanoates," *Microbiological Reviews* pp. 450–472 (1990).

Bailey, "Free radical ring–opening polymerization," *J. Polym. Preprints* 25:210–11 (1984).

Bailey, et al., "Synthesis of Poly–ϵ–caprolactone via a free radical mechanism. Free radical ring–opening polymerization of 2–methylene–1,3–dioxepane," *J. Polym. Sci. Polym. Chem.* 20:3021–30 (1982).

Braunegg, et al., "Polyhydroxyalkanoates, biopolyesters from renewable resources: physiological and engineering aspects," *J. Biotech.* 65: 127–161 (1998).

Bruhn & Muller, "Preparation and characterization of spray–dried Poly(DL–Lactide) Micro Spheres," *Proceed. Intern. Symp. Control. Rel. Bioact. Mater.* 18:668–69 (1991).

Byrom, "Miscellaneous Biomaterials," in *Biomaterials* (D. Byrom, ed.) pp. 333–359 MacMillan Publishers: London, 1991.

Conti, et al., "Use of polyactic acid for the preparation of microparticulate drug delivery systems," *J. Microencapsulation* 9:153–166 (1992).

Cookson, "It grows on trees," *Financial Times* p. 6 (Aug. 12, 1992).

De Groot, "Meniscal tissue regeneration in porous 50/50 copoly(L–lactide/epsilon–caprolactone) implants," *Biomaterials* 18(8):613–22 (1997).

De Smet, et al., "Characterization of intracellular inclusions formed by *Pseudomonas oleovorans* during growth on octane," *J. Bacteriol.* 154:870–78 (1983).

DuBois, et al., "Macromolecular Engineering of Polylactones and Polylactides. 12. Study of the Depolymerization Reactions of Poly (ϵ–caprolactone) with Functional Aluminum Alkoxide End Groups," *Macromolecules* 26:4407–12 (1993).

Duvernoy, et al. "A biodegradable patch used as a pericardial substitute after cardiac surgery: 6–and 24–month evaluation with CT," *Thorac. Cardiovasc. Surg.* 43(5):271–74 (1995).

Fukuzaki, et al., "Direct copolymerization of L–lactic acid with γ–butyrolactone in the absence of catalysts," *Die Madromoleculare Chemie* 190:1553–59 (1989).

Gagnon, et al., "A thermoplastic elastomer produced by the bacterium *Pseudomonas oleovarans*," *Rubber World* 207:32–38 (1992).

Gagnon, et al., "Chemical modification of bacterial elastomers: 1. Peroxide crosslinking," *Polymer* 35:4358–67 (1994).

Gerngross & Martin, "Ezyme–catalyzed synthesis of poly [(R)–(–)–3–hydroxybutyrate]: formation of macroscopic granules in vitro," *Proc. Natl. Acad. Sci. USA* 92:6279–83 (1995).

Gross, et al., "Polymerization of β–Monosubstituted–β–propiolactones Using Trialkylaluminum–Water Catalytic Systems and Polymer Characterization," *Macromolecules* 21:2657–68 (1988).

Hocking & Marchessault, "Syndiotactic poly[(R, S)–β–hydroxybutyrate] isolated from methyaluminoxane–catalyzed polymerization," *Polym. Bull.* 30:163–70 (1993).

Hocking & Marchessault, "Biopolyesters" in *Chemistry and Technology of Biodegradable Polymers*, (G.J.L. Griffin, ed.), pp. 48–96, Chapman and Hall: London, 1994.

Holmes, "Biologically Produced (R) 3–hydroxyalkanoate Polymers and Copolymers," in *Developments in Crystalline Polymers* (Bassett, ed.), pp. 1–65, Elsevier: London, 1988.

Hori, et al., "Chemical synthesis of high molecular weight poly(3–hydroxybutyrate–co–4–hydroxybutyrate)," *Polymer* 36:4703–05 (1995).

Hori, et al., "Ring–Opening Copolymerization of Optically Active β–Butyrolactone with Several Lactones Catalyzed by Distannoxane Complexes: Synthesis of New Biodegradable Polyesters," *Macromolecules* 26:4388–90 (1993).

Hori, et al., "Ring–Opening Polymerization of Optically Active β–Butyrolactone Using Distannoxane Catalysts: Synthesis of High Molecular Wright Poly(3–hydroxybutyrate)," *Macromolecules* 26:5533–34 (1993).

Hutmacher, et al., "A review of material properties of biodegradable and bioresorbable polymers and devices for GTR and GBR applications," *Int. J. Oral Maxillofac. Implants* 11(5):667–78 (1996).

Keeler, "Don't Let Food Go To Waste—Make Plastic Out of It," *R&D Magazine* pp. 52–57 (1991).

Keeler, "Plastics Grown in Bacteria Inch Toward the Market," *R&D Magazine* pp. 46–52 (1991).

Kemnitzer, et al., "Preparation of predominantly Syndiotactic Poly(β–hydroxybutyrate) by the Tributylin Methoxide Catalyzed Ring–Opening Polymerization of racemic β–Butyrolactone," *Macromolecules* 26: 1221–29 (1993).

Kishida, et al., "Formulation–assisted biodegradable polymer matrices," *Chemical and Pharmaceutical Bulletin* 37:1954–56 (1989).

Koosha, "Preparation and characterization of biodegradable polymeric drug carriers," Ph.D. Dissertation, 1989, Univ. Nottingham, UK., *Diss. Abstr. Int. B* 51:1206 (1990).

Koosha, et al., "Polyhydroxybutyrate as a drug carrier," *Crit. Rev. Ther. Drug Carrier Syst.* 6(2):117–30 (1989).

Korte & Gelt, "Hochdruckreaktionen. II. Die Polymerization Von γ butyrolacton und δ–valerolactam bei hohen drücken," *Polymer Lett.* 4:685–89 (1966).

Kusaka, et al., "Microbial synthesis and Physical Properties of ultra–high–molecular–weight poly(R)–3–hydroxybutyrate," *Pure Appl. Chem.* A35:319–35 (1998).

Lafferty, et al., "Microbial Production of Poly–b–hydroxybutyric acid" in *Biotechnology* (Rehm & Reed, Eds.), pp. 135–76, Verlagsgesellschaft:Weinheim, 1988.

Lamba, et al., "Degradation of polyurethanes," in *Polyurethanes in Biomedical Applications* (CRC Press:Boca Raton, Florida, 1998).

Le Borgne, et al., "Stereoelective polymerization of β–butyrolactone," *Polymer* 30:2312–19 (1989).

Lee, et al., "Copolymerization of γ–butyrolactone and β–butyrolactone," *Macromol. Chem. Phys.* 198:1109–20 (1997).

Lemoigne & Roukhelman, "Fermetation β–Hydroxybutyrique Caracterisation et Evolution Des Produits de Deshydration et de Polymerisation de L'acide β–Dehydroxybutyrique," *Annales des fermentations*, 5:527–36 (1925).

Lloyd, et al., "Transformation of *Arabidopsis thalania* with *Agrobacterium tumefaciens,*" *Science* 234: 464–66 (1986).

Madison & Huisman, "Metabolic engineering of poly(3–hydroxyalkanoates): from DNA to plastic," *Microbiol. Molec. Biol. Rev.* 63:21–53 (1999).

Malm, et al., "A new biodegradable patch for closure of atrial septal defect. An experimental study," *Scand. J. Thorac. Cardiovasc. Surg.* 26(1):9–14 (1992).

Malm, et al., "Enlargement of the right ventricular outflow tract and the pulmonary artery with a new biodegradable patch in transannular position," *Eur. Surg. Res.* 26(5):298–308 (1994).

Malm, et al., "Prevention of postoperative pericardial adhesions by closure of the pericardium with absorbable polymer patches. An experimental study," *J. Thorac. Cardiovasc. Surg.* 104(3):600–07 (1992).

Mathiowitz & Langer, "Polyanhydride microspheres as drug delivery systems" in *Microcapsules Nanopart. Med. Pharm.* (Donbrow, ed.), pp. 99–123 (CRC:Boca Raton, Florida, 1992).

Maysinger, et al., "Microencapsulation and the Grafting of Genetically Transformed Cells as Therapeutic Strategies to rescue Degenerating Neurons of the CNS," *Reviews in the Neurosciences*, 6:15–33 (1995).

McMillin, et al., "Elastomers for Biomedical Applications," *Rubber Chemistry and Technology* 67:417–446 (1994).

Muller, et al., "Poly(hydroxyalkanoates): A Fifth Class of Physiologically Important Organic Biopolymers," *Angew. Chem. Int. Ed. Engl.* 32: 477–502 (1993).

Nakamura, et al., "Microbial synthesis and characterization of poly(3–hydroxybutyrate–co–4–hydroxybutyrate)," *Macromol.* 25:4237–41 (1992).

Nobes, et al., "Polyhydroxyalkanoates: Materials for delivery systems," *Drug Del.* 5:167–77 (1998).

Ogawa, et al., "A New Technique to Efficiently Entrap Leuprolide Acetate into Microcapsules of Poly Lactic Acid or Copoly(Lactic/Glycolic) Acid," *Chem. Pharm. Bull.* 36:1095–103 (1988).

Otera, et al., "Distannoxane as reverse micelle–type catalyst: novel solvent effect on reaction rate of transesterification," *J. Org. Chem.* 54:4013–14 (1989).

Otera, et al., "Distannoxane–catalysed transesterification of 1,n–Dioldiacetates. Selective transformation of either of chemically equivalent functional groups," *J. Chem. Soc. Chem. Commun.* 1742–43 (1991).

Otera, et al., "Novel distannoxane–catalyzed transesterification and a new entry to α,β–unsaturated carboxylic acids," *Tetrahedron Lett.*, 27:2383–86 (1986).

Otera, et al., "Novel template effects of distannoxanne catalysts in highly efficient transesterification and esterification," *J. Org. Chem.* 56:5307–11 (1991).

Peoples, et al., "Poly–β–hydroxybutyrate Biosynthesis in *Alcaligenes eutrophus* H16," *J. Biol. Chem* 264(26):15293–97 (1989).

Peoples, et al., "Polyhydroxybutyrate (PHB): A Model System for Biopolymer Engineering II," in *Novel Biodegradable Microbial Polymers* (Dawes, ed.) pp. 191–202, Kluwer Academic Publishers:Netherlands (1990).

Perrin & English, "Polycaprolactone," in *Handbook of Bioabsorbable Polymers* (Domb, et al., eds.) pp. 63–77 (Harwood, Amsterdam, 1997).

Poirier, "Perspectives on the production of polyhydroxyalkanoates in plants," *FEMS Microbiology Reviews* 103:237–46 (1992).

Poirier, et al., "Progress Toward Biologically Produced Biodegradable thermoplastics," *Adv. Mater.* 5(1):30–37 (1993).

Pool, "In Search of the Plastic Potato," *Science* 245: 1187–89 (1989).

Pouton & Akhtar, "Biosynthetic polyhydroxyalkanoates and their potential in drug delivery," *Adv. Drug Delivery Rev.* 18:133–62 (1996).

Rivard, et al., "Fibroblast seeding and culture in biodegradable porous substrates," *J. Appl. Biomater.* 6(1):65–68 (1995).

Saito, et al., "Microbial synthesis and properties of poly(3–hydroxybutyrate–co–4–hydroxybutyrate) in *Comamonas acidovorans,*" *Int. J. Biol. Macromol.* 16(2):99–104 (1994).

Schwartz & Goodman, *Plastic Materials and Processes*, (Van Nostrand Reinhold Company:New York, 1982).

Shin'oka & Mayer, "New frontiers in tissue engineering: tissue engineered heart valves" in *Synthetic Bioabsorbable Polymer Scaffolds* (Atala & Mooney, eds.) pp. 187–198 Birkhäuser Boston, 1997.

Sim, et al., "PHA synthase activity controls the molecular weight and polydispersity of polyhydroxybutyrate in vivo," *Nat. Biotechnol.* 15(1):63–67 (1997).

Stanton & Gagne, "The remarkable catalytic activity of alkali–metal alkoxide clusters in the ester interchange reaction," *J. Am. Chem. Soc.* 119:5075–76 (1997).

Steinbuchel & Valentin, "Diversity of bacterial polyhydroxyalkanoic acids," *FEMS Microbiol. Lett.* 128:219–28 (1995).

Steinbuchel & Wiese, "*A Pseudomonas* strain accumulating polyesters of 3–hydroxybutyric acid and medium–chain–length 3–hydroxyalkanoic acids," *Appl. Microbiol. Biotechnol.* 37:691–97 (1992).

Steinbuchel, "Polyhydroxyalkanoic Acids," in *Biomaterials* (D. Byrom ed.), pp. 123–213, MacMillan Publishers: London, 1991.

Steinbuchel, "Molecular basis for biosynthesis and accumulation of polyhydroxyalkanoic acids in bacteria," *FEMS Microbiol. Rev.* 103:217–230 (1992).

Tanahashi, et al., "Thermal Properties and Stereoregularity of Poly(3–hydroxybutyrate) Prepared from optically Active β–Butyrolactone with a Zinc–Based Catalyst," *Macromolecules* 24:5732–33 (1991).

Valentin, et al., "Identification of 5–hydroxyhexanoic acid, 4–hydroxyaheptanoic acid and 4–hydroxyoctanoic acid as new constituents of bacterial polyhydroxyalkanoic acids," *Appl. Microbiol. Biotechnol.* 46:261–67 (1996).

Valentin, et al., "Identification of 4–hydroxyhexanoic acid as a constituent of biosynthetic polyhydroxyalkanoic acids from bacteria," *Appl. Microbiol. Biotechnol.* 36:507–514 (1994).

Valentin, et al., "Identification of 4–hydroxyhexanoic acid as a new constituent of biosynthetic polyhydroxyalkanoic acids from bacteria," *Appl. Microbiol. Biotechnol.* 40:710–16 (1994).

Wallen & Rohwedder, "Poly–β–hydroxyalakaonate from Activated Sludge," *Environ. Sci. Technol.* 8:576–79 (1974).

Williams & Peoples, "Biodegradable plastics from plants," *Chemtech* 26:38–44 (1996).

Williams & Peoples, "Making plastics green," *Chem. Br.* 33:29–32 (1997).

Williams, et al., "PHA applications: addressing the price performance issue. I. Tissue engineering," *Int. J. Biol. Macromol.* 25(1–3): 111–121 (1999).

Wong & Mooney, "Synthesis and properties of bioabsorbable polymers used as synthetic matrices for tissue engineering," in *Synthetic Bioabsorbable Polymer Scaffolds* (Atala, et al., eds.) pp. 51–82 (Birkhäuser: Boston, 1997).

Xie, et al., "Ring–opening Polymerization of β–Butyrolactone by Thermophilic Lipases," *Macromolecules* 30:6997–98 (1997).

\* cited by examiner

P3HB: poly-R-3-hydroxybutyrate; P4HB: poly-4-hydroxybutyrate; P3HB4HB: poly-R-3-hydroxybutyrate-co-4-hydroxybutyrate; P3HO3HH: poly-R-3-hydroxyoctanoate-co-3-hydroxyhexanoate.

BIOABSORBABLE, BIOCOMPATIBLE POLYMERS FOR TISSUE ENGINEERING

CROSS-REFERENCE TO RELATED APPLICATIONS

This application is a divisional of U.S. Ser. No. 09/518,123, now U.S. Pat. No. 6,514,515 filed Mar. 3, 2000, which claims priority of.

Priority is claimed to U.S. provisional application Serial No. 60/122,827, filed Mar. 4, 1999.

FIELD OF THE INVENTION

The present invention generally relates to bioabsorbable, biocompatible polymers and methods for making devices for tissue engineering and tissue regeneration from these materials.

BACKGROUND TO THE INVENTION

During the last 20 to 30 years, several bioabsorbable, biocompatible polymers have been developed for use in medical devices, and approved for use by the U.S. Food and Drug Administration (FDA). These FDA approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). In general, these materials biodegrade in vivo in a matter of months, although certain more crystalline forms biodegrade more slowly. These materials have been used in orthopedic applications, wound healing applications, and extensively in sutures after processing into fibers. More recently, some of these polymers also have been used in tissue engineering applications.

Tissue engineering has emerged as a multi-disciplinary field combining biology, materials science, and surgical reconstruction, to provide living tissue products that restore, maintain, or improve tissue function. The need for this approach has arisen primarily out of a lack of donor organs and tissues, but also because it offers the promise of being able to dramatically expand the ability to repair tissues and develop improved surgical procedures.

In general, three distinct approaches currently are used to engineer new tissue. These are (1) infusion of isolated cells or cell substitutes, (2) use of tissue inducing materials and/or tissue regeneration scaffolds (sometimes referred to as guided tissue repair), and (3) implantation of cells seeded in scaffolds (either prior to or subsequent to implantation). In the third case, the scaffolds may be configured either in a closed manner to protect the implanted cells from the body's immune system, or in an open manner so that the new cells can be incorporated into the body.

In open scaffold systems and guided tissue repair, tissue engineering devices have normally been fabricated from natural protein polymers such as collagen, or from the synthetic polymers listed above, which in both cases degrade over time and are replaced by new tissue. While some of these materials have proven to be good substrates for cell and tissue growth, and provide good scaffolding to guide and organize the regeneration of certain tissues, they often do not have the specific mechanical requirements that the scaffold needs to provide until the new tissue is developed and able to take over these functions. These materials may also be difficult to process and fabricate into the desired form, handle poorly in the operating room, be difficult to suture, and sometimes fall apart prematurely. For example, it has been reported that tissue engineered heart valve leaflet scaffolds derived from polyglactin and PGA are too stiff and cause severe pulmonary stenosis when implanted in sheep (Shinoka, et al., "New frontiers in tissue engineering: tissue engineered heart valves" in *Synthetic Bioabsorbable Polymer Scaffolds* (Atala & Mooney, eds.) pp. 187–98 (Birkhäuser, Boston, 1997)).

FIG. 1, which plots the tensile strength and elongation to break values for representative FDA approved (compression molded) bioabsorbable biocompatible polymers against these values for different tissue structures, reveals a significant mismatch between the mechanical properties of these polymers and the different tissue structures. In particular, it is apparent that the existing bioabsorbable biocompatible polymers are stiff, inelastic materials, with elongations to break of around 25%, yet many tissues are much more flexible, elastic, and have longer elongation to break values. Accordingly, the biomaterial products currently used in temporary scaffolds for regenerating human tissues do not exhibit the same multi-axial physical and mechanical properties as native tissues, which are hierarchical, three-dimensional structures (see abstract of an award by the Advanced Technology Program to Johnson and Johnson Corporate Biomaterials Center, October 1997).

Attempts have been made to develop new bioabsorbable biocompatible polymers with more flexible, elastomeric properties. One approach has been to incorporate lactide or glycolide and caprolactone joined by a lysine-based diisoyanate into a polyurethane (Lamba, et al., "Degradation of polyurethanes" in *Polyurethanes in Biomedical Applications*, pp.199–200 (CRC Press LLC, Boca Raton, Fla., 1998). However, these crosslinked polyurethane networks cannot be processed by standard techniques such as solution casting or melt processing, limiting their usefulness. There is also no evidence that the polyurethane segments are completely biodegraded in vivo. A commercial material, known as TONE™, has also been evaluated as an elastomeric implant material. However, this material degrades in vivo very slowly, and therefore has limited application (Perrin, et al., "Polycaprolactone" in *Handbook of Bioabsorbable Polymers* (Domb, et al., eds.) pp.63–76 (Harwood, Amsterdam, 1997)). Another approach has been to synthesize protein-based polymers, particularly polymers containing elastomeric polypeptide sequences (Wong, et al., "Synthesis and properties of bioabsorbable polymers used as synthetic matrices for tissue engineering" in *Synthetic Bioabsorbable Polymer Scaffolds* (Atala & Mooney, eds.) pp.51–82 (Birkhäuser, Boston, 1997). However, these materials are not reported to biodegrade in vivo, although cells can invade matrices derived from these materials. They also lack the advantages of thermoplastic polymers in fabrication of devices.

U.S. Pat. Nos. 5,468,253 and 5,713,920, both to Bezwada et al., disclose bioabsorbable elastomeric materials which are used to form devices that, based on in vitro data, are alleged to completely bioabsorb within one year or six months. However, deGroot et al., Biomaterials, 18:613–22 (1997) provides in vivo data for these materials and reports that the implanted material fragmented after 56 weeks into white crystalline-like fragments. It is suspected that these fragments are crystalline poly-L-lactide, which is very slow to degrade. Nonetheless, whatever the composition of the fragments, the material is not completely bioabsorbed after one year in vivo. These materials also typically are difficult to process and may have poor shelf stability.

Thus, while the current bioabsorbable biocompatible polymers offer a range of useful properties for certain medical applications, it is desirable to develop methods to prepare bioabsorbable biocompatible polymers that significantly extend the range of properties available. It would thus be desirable to develop methods for preparing bioabsorbable biocompatible polymers with mechanical properties closer to those of tissue, particularly soft tissues. It would also be desirable to develop methods for making bioabsorbable biocompatible materials which can be readily processed, and fabricated into tissue engineering devices that can be easily implanted.

It is therefore an object of this invention to provide methods for preparing bioabsorbable biocompatible polymers with mechanical properties that provide a better match with those of tissue structures.

It is a further object of this invention to provide new compositions with mechanical properties that provide a better match with those of tissue structures.

It is another object of this invention to provide methods for fabricating devices from these compositions.

SUMMARY OF THE INVENTION

Bioabsorbable biocompatible polymers are selected based on their physical and/or mechanical properties to correspond to the physical properties of tissues to be regenerated or constructed. Physical properties include elasticity, strength, flexibility, and processibility. These properties can be measured by determining factors such as tensile strength, elongation or extension to break, and Youngs modulus. In a preferred embodiment, the polymers have an extension to break over 25%, tensile strength less than 10,000 psi, Youngs modulus less than 100,000 psi, glass transition temperature less than 20° C., and melting temperature less than 190° C. In one embodiment, the bioabsorbable biocompatible polymers can be prepared with tensile strengths equivalent to the tensile strengths of the tissues of the cardiovascular, gastrointestinal, kidney and genitourinary, musculoskeletal, and nervous systems, as well as those of the oral, dental, periodontal, and skin tissues. In another embodiment, the bioabsorbable biocompatible polymers can be prepared with elongations to break equivalent to the elongations to break of the same tissues. In still another embodiment, the bioabsorbable biocompatible polymers can be prepared with tensile modulus (Young's modulus) values equivalent to these tissues.

Methods for processing the bioabsorbable biocompatible polymers into tissue engineering devices are also described.

DETAILED DESCRIPTION OF THE INVENTION

Figure 1:
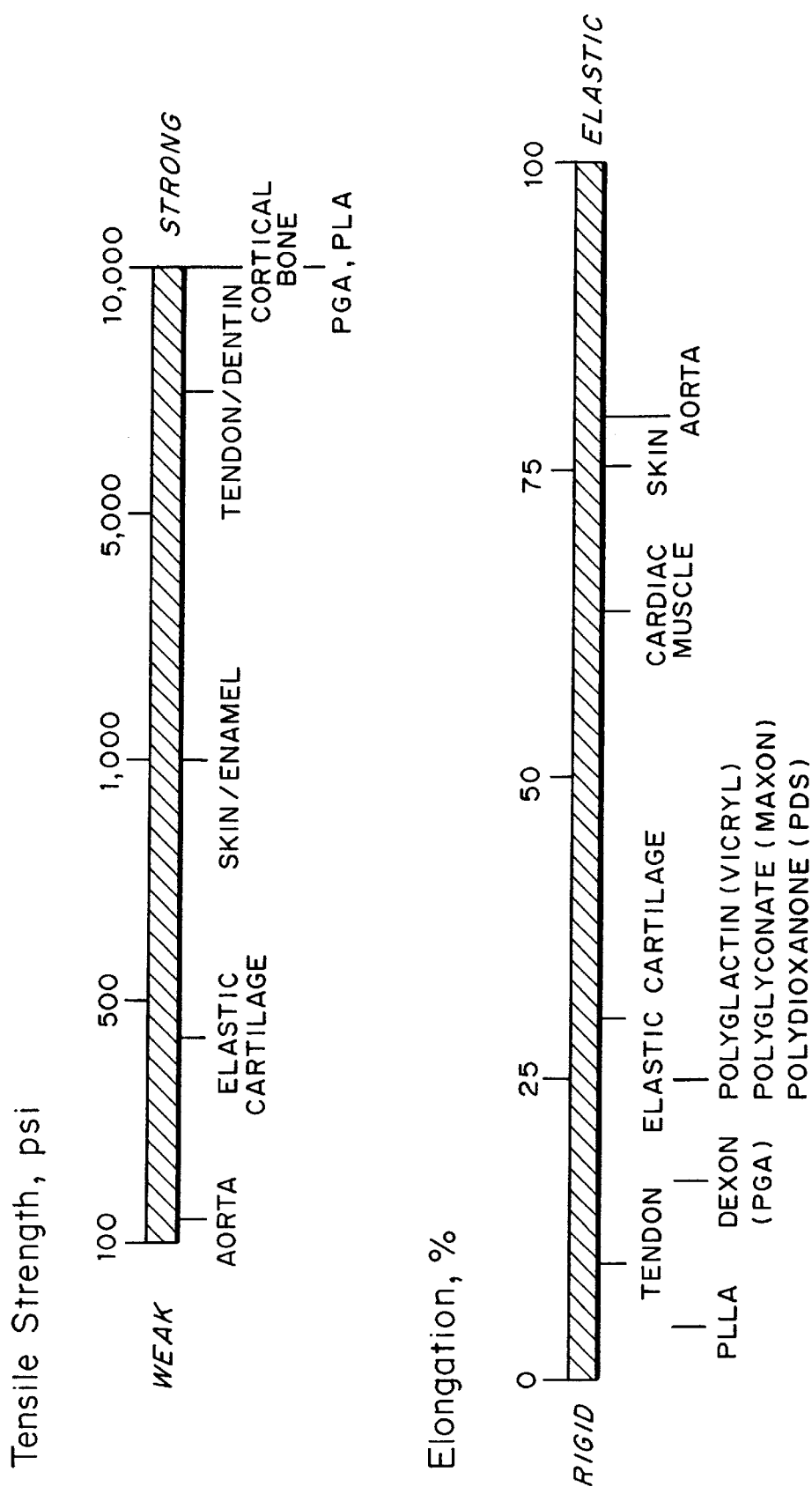
FIG. 1 is a graph comparing the mechanical properties of PGA, PLA, polyglactin, polyglyconate, and polydioxanone with those of different tissue structures.
Figure 2:
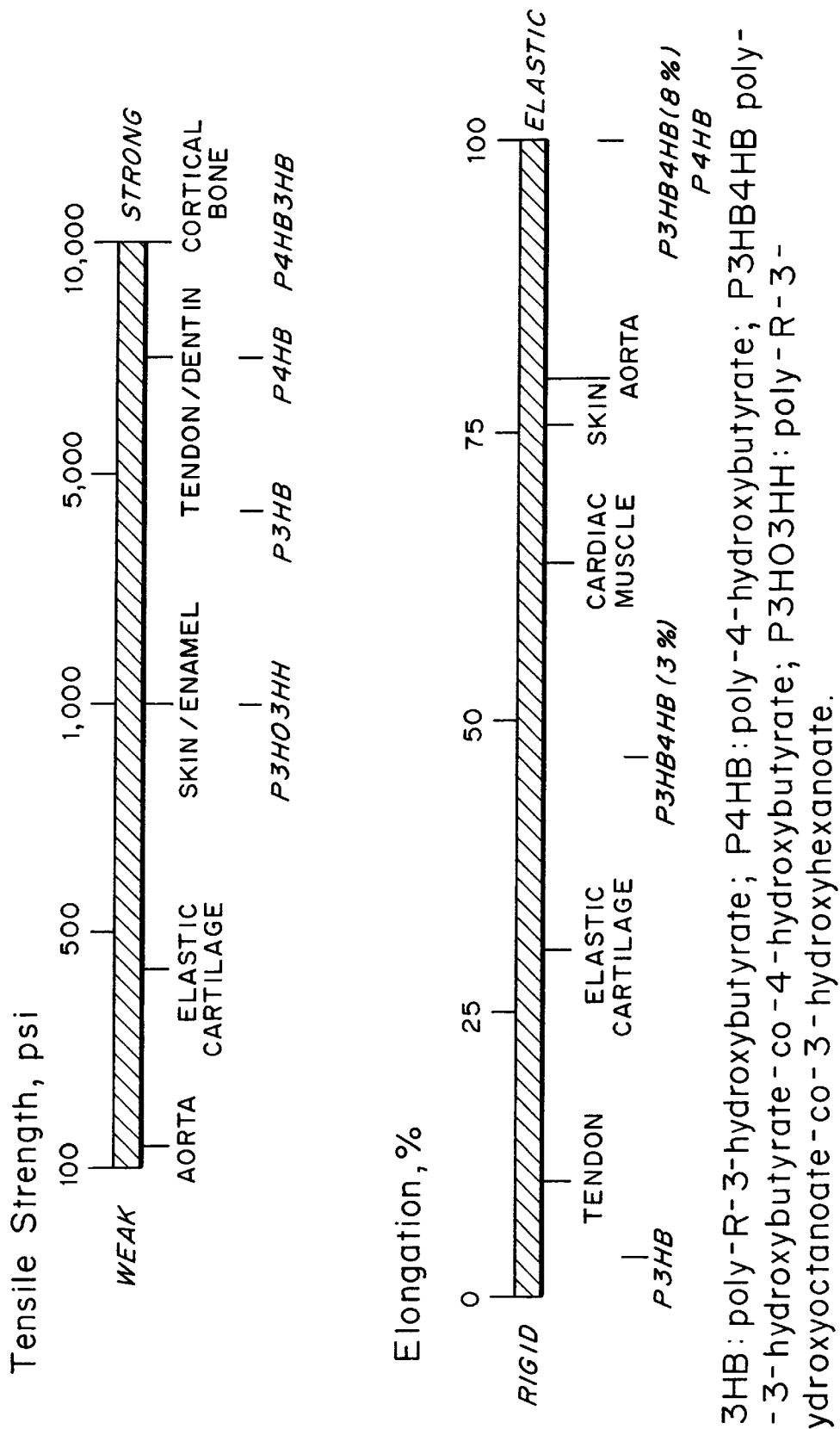
FIG. 2 is a graph comparing the mechanical properties of bioabsorbable polymers described herein with the mechanical properties of different tissues or tissue structures.

Polymers are provided which are bioabsorbable, biocompatible, and have mechanical properties similar to the physical and/or mechanical properties of tissue structures, including stress, strain, stress-strain, stress-strain hysteresis, stress-strain relaxation, viscoelasticity, contraction stress, resting stress, Young's modulus, tensile strength, durability, yield point, failure strength, toughness, ductility, softness, hardness, creep, elastic deformation, wear resistance, shear failure, roughness, compressive strength, load capacity, modulus of elasticity, ultimate compressive strength, yield strength, stress-strain relationship, scratch resistance, abrasion resistance, flexural modulus, shear modulus, contact angle, surface tension, adhesive strength, surface free energy, bending strength, shear strength, bonding strength, bending strength, bending stiffness, compressive modulus, bending modulus, fracture toughness, elongation, fiber strength, fiber modulus, fiber elongation, thermal expansion coefficient, fracture toughness, static and dynamic elasticity, longitudinal stretch, stress, and strain, radial stretch, stress and strain, circumferential stretch, stress and strain, ultimate elongation, viscosity, expansion, static and kinetic coefficients of friction, plasticity, axial tension, shock absorbance, bearing strength, formability, rigidity, stress rupture, bend radius, impact strength, and fatigue strength. In a preferred embodiment, the polymers have elongations to break of more than 25%, and/or tensile modulus values less than 500,000 psi. In another preferred embodiment, the polymers are fabricated into medical devices using standard polymer processing techniques, and used as tissue engineering devices to provide living tissue products that restore, maintain, or improve tissue function, for example, in the cardiovascular, gastrointestinal, kidney and genitourinary, musculoskeletal, and nervous systems, as well as those of the oral, dental, periodontal, and skin tissues.

I. Polymers

The polymers described herein may be prepared by synthetic or natural methods. However, the method must provide the desired polymer in a form sufficiently pure for use as an implantable material. The polymer should not contain any undesirable residues or impurities which could elicit an undesirable response either in vitro in the case of a cell-seeded construct or in vivo.

The polymers may be prepared from any combination of monomeric units. These units must, however, be capable of biodegrading in vivo to nontoxic compounds, which can optionally be excreted or further metabolized. The combination of units in the polymer must also be biocompatible, and not elicit an undesirable biological response upon implantation. The polymer may be biodegraded in vivo by any means, including hydrolysis, enzymatic attack, a cell-mediated process, or by any other biologically mediated process. It is considered desirable for tissue engineering applications that the polymer scaffold serve as a transitional construct, and thus be fully degraded once the new tissue is able to take over the function of the scaffold. Since the rates at which different new tissues are likely to be able to assume their new function will vary, it is desirable to have polymers with a range of degradation rates as well as a range of different properties. Generally, however, preferred polymers will degrade in a matter of weeks to months, preferably less than one year, rather than several years.

The mechanical properties of the polymer are designed to meet the needs of the particular tissue engineering application. Thus, according to the method described herein for preparing bioabsorbable biocompatible polymers, the monomeric units can be selected to provide upon combination of the correct ratios of these monomeric units the desired property or property set. If necessary, the monomeric units may be combined in a specific order as in, for example, a block copolymer, or alternatively they can be assembled in a random manner. They may also be prepared with different molecular weights to achieve the correct performance.

In a preferred method as described herein, the monomeric units are hydroxy acids, and the polymers are polyesters.

The distance between the hydroxy group and the acid group can be small or large, however, monomers are preferably 2-, 3-, 4-, 5-, or 6-hydroxy acids. The hydroxy acids may optionally contain other functional groups and be substituted at any position, including heteroatoms between the hydroxy and acid groups. These hydroxy acids may be polymerized either using synthetic methods or preferably using biological methods. In the latter case, the hydroxy acids may be derived in vivo from a non-hydroxy acid source.

Suitable methods for preparing the polyesters are described in Williams, S. F. and Peoples, O. P. *CHEMTECH* 26:38–44 (1996), Williams, S. F. and Peoples, O. P., *Chem. Br.*, 33:29–32 (1997), U.S. Pat. No. 4,910,145 to Holmes, P. A. and Lim, G. B.; Byrom, D., "Miscellaneous Biomaterials," in D. Byrom, Ed., "Biomaterials" MacMillan Publishers, London, 1991, pp. 333–59; Hocking, P. J. and Marchessault, R. H. "Biopolyesters", G. J. L. Griffin, Ed., "Chemistry and Technology of Bioabsorbable Polymers," Chapman and Hall, London, 1994, pp. 48–96; Holmes, P. A., "Biologically Produced (R)-3-hydroxyalkanoate Polymers and Copolymers," in D. C. Bassett Ed., "Developments in Crystalline Polymers," Elsevier, London, Vol. 2, 1988, pp. 1–65; Lafferty et al., "Microbial Production of Poly-β-hydroxybutyric acid," H. J. Rehm and G. Reed, Eds., "Biotechnology", Verlagsgesellschaft, Weinheim, Vol. 66, 1988, pp. 135–76; Müller and Seebach, *Angew. Chem. Int. Ed. Engl.* 32:477–502 (1993); Steinbüchel, A. "Polyhydroxyalkanoic Acids," in D. Byrom Ed., "Biomaterials", MacMillan Publishers, London, 1991, pp. 123–213; Steinbüchel and Wiese, *Appl. Microbiol. Biotechnol*, 37:691–697 (1992); U.S. Pat. Nos. 5,245,023; 5,250,430; 5,480,794; 5,512,669; 5,534,432; Agostini, D. E. et al., *Polym. Sci.*, Part A-1, 9:2775–87 (1971); Gross, R. A. et al., *Macromolecules*, 21:2657–68 (1988); Dubois, P. I. et al., *Macromolecules*, 26:4407–12 (1993); Le Borgne, A. and Spassky, N., *Polymer*, 30:2312–19 (1989); Tanahashi, N. and Doi, Y., *Macromolecules*, 24:5732–33 (1991); Hori, Y. M. et al., *Macromolecules*, 26:4388–90 (1993); Kemnitzer, J. E. et al., *Macromolecules*, 26:1221–1229 (1993); Hori, Y. M. et al., *Macromolecules*, 26:5533–34 (1993); Hocking, P. J. and Marchessault, R. H., *Polym. Bull.*, 30:163–70 (1993); Xie, W. et al., *Macromolecules*, 30:6997–98 (1997), U.S. Pat. No. 5,563,239 to Hubbs, J. C. and Harrison, M. N., and Braunegg, G. et al., *J Biotechnol.* 65: 127–61 (1998), and Madison & Huisman, *Microb. Mol. Biol. Rev.* 63:21–53 (1999).

In another preferred method described herein, the bioabsorbable biocompatible polymers are polyesters including one or more linkages in the main polymer chain which are not ester linkages. These linkages should be susceptible to cleavage in vivo. Suitable non-ester linkages may include amides, urethanes, carbonates, iminocarbonates, oxalates, oxamates, orthoesters, anhydrides, phosphazenes, glycosides, and ethers. Incorporation of such chemistries can be used to alter biodegradation rates, tailor mechanical, surface, or other properties of the polymer, improve processibility and handling of the materials, and/or to provide methods for attachment of other compounds to the polymers.

The bioabsorbable biocompatible polymers described herein may optionally be further modified either prior to or subsequent to fabrication. Representative modifications include derivatization, surface treatments, coatings, coupling of other compounds particularly biologically active agents.

II. Mechanical Properties and Polymer Compositions

The bioabsorbable biocompatible polymers described herein may be prepared with mechanical properties that resemble those of tissue. These properties are achieved by preparing the polymers with different compositions and ratios of monomeric constituents. For example, polymers with tensile strengths near or equal to that of tendon and dentin can be prepared by polymerizing 4-hydroxybutyric acid. By incorporating R-3-hydroxybutyric acid with 4-hydroxybutyric acid into the same polymer as a random copolymer, it is possible to prepare a material with a tensile strength near or equal to that of cortical bone. Using combinations of R-3-hydroxyoctanoate and R-3-hydroxyhexanoate, it is possible to prepare a copolymer with a tensile strength near or equal to that of skin and enamel. Other monomers may be incorporated to increase or decrease the tensile strengths of the bioabsorbable biocompatible polymers.

The elongation to break of the bioabsorbable biocompatible polymers may also be controlled and tailored to those of tissue in a similar manner. For example, the homopolymer of R-3-hydroxybutyric acid has an elongation to break of around 5%, close to tendon. This elongation to break may be progressively increased to values for cartilage, cardiac muscle, cardiovascular tissues, skin, aorta, urological tissue, in fact virtually any tissue, by incorporating a co-monomer, 4-hydroxybutyric acid, with R-3-hydroxybutyric acid into a copolymer. A copolymer comprising 3–8% 4-hydroxybutyric acid polymerized with 3-hydroxybutyric acid has an extension to break of 45% to over 100%, which are similar values to those of cardiac muscle, skin, urological and cardiovascular tissues including blood vessels and heart valves.

In the same manner, it is also possible to prepare bioabsorbable biocompatible polymers described herein with a range of tensile modulus values (Youngs modulus) that match those of tissue structures. For example, depending upon the age of the person, skin has a tensile modulus value ranging from about 2,000 psi for young children to around 18,000 psi for older people. According to the method described herein, it is possible to produce a copolymer of R-3-hydroxyoctanoic acid and R-3-hydroxyhexanoic acid with a Youngs modulus value of around 1,000–2,000 psi, and a copolymer of R-3-hydroxybutyric acid and 4-hydroxybutyric acid with a Youngs modulus ranging from 3,000 psi to 22,000 psi as the percentage of 4-hydroxybutyric acid is increased from 78% to 100%. Other compositions can be used for applications requiring higher Youngs modulus values. For example, the homopolymer of R-3-hydroxybutyric acid has a Youngs modulus value of around 500,000 psi. Thus, by using combinations of different hydroxy acid monomers, it is possible to prepare bioabsorbable biocompatible polymers with a wide range of Youngs modulus values that encompass different tissue structures.

By using a similar approach of combining appropriate monomer units, bioabsorbable biocompatible polymers can be produced that have other desirable mechanical properties and even desirable barrier properties that provide a good compliance match with tissue. Examples of other mechanical properties which can be prepared according to the method described herein include, but are not limited to, compressive strength, hardness, burst strength, impact strength, toughness, as well as other viscoelastic elastic properties. Examples of desirable barrier properties include water and fluid barrier properties, moisture vapor barrier properties, and gas barrier properties.

In some embodiments, it may be desirable to produce a bioabsorbable biocompatible polymer with two or more mechanical properties providing a good compliance match with a specific tissue structure. For example, tendon has a tensile strength of around 6,000 psi and an elongation to break of 10%. According to the method described herein, a bioabsorbable biocompatible polymer can be produced comprising 10% R-3-hydroxypentanoic acid and R-3-hydroxybutyric acid, with approximately the same tensile strength of about 6,000 psi and an extension to break of 10% as tendon. Similarly, other combinations of one, two, or more monomeric units can be used to provide bioabsorbable biocompatible polymers with two or more of the desired mechanical properties of a particular tissue structure.

III. Fabrication of Bioabsorbable Biocompatible Devices

The bioabsorbable biocompatible polymer compositions are useful for preparing a variety of medical devices. Examples of applications of such devices include tissue engineering scaffold, guided tissue repair material, wound dressing, drug delivery vehicle, anti-adhesion material, cell encapsulation material, coating, implant, stent, orthopaedic device, prosthetic, adhesives, diagnostics, sutures, surgical meshes, staples, meniscus repair and regeneration devices, screws (interference screws and meniscal screws), bone plates and plating systems, cardiovascular patches, pericardial patches, slings, pins, anti-adhesion barriers, articular cartilage repair devices, nerve guides, tendon and ligament repair devices, atrial skeletal defect patches, bulking and filling agents, vein valves, bone marrow scaffolds, bone graft scaffolds, skin substitutes, dural substitutes, ocular implants, spinal fusion cages, and muscular implants (cardiac and skelatal). These materials may be used alone, with additives or in combinations with themselves or other materials. Additives and other materials may include those components added for the purpose of further modification of a particular property or properties, and/or those components which are biologically active such as cell attachment factors, growth factors, peptides, antibodies and their fragments.

In general, a key advantage described herein is that the bioabsorbable biocompatible polymers can be processed using conventional polymer processing techniques. Many of the materials are thermoplastics, and are thus amenable to standard methods for processing such materials. Such methods are well known to those skilled in the art, and include such methods as melt processing, solvent processing, leaching, foaming, extrusion, injection molding, compression molding, blow molding, spray drying, extrusion coating, spinning of fibers and subsequent processing into woven or non-woven constructs.

A preferred fabricated form of the compositions is a porous (fibrous) construct, particularly ones which can be used as tissue engineering scaffolds, and guided tissue repair meshes and matrices. This construct or matrix may be derived by any suitable method, including salt leaching, sublimation, solvent evaporation, spray drying, foaming, processing of the materials into fibers and subsequent processing into woven or non-woven devices. Such constructs can be used in tissue engineering applications of the tissues of the cardiovascular, gastrointestinal, kidney and genitourinary, musculoskeletal, and nervous systems, as well as those of the oral, dental, periodontal, and skin tissues. Examples of such constructs can be used to prepare tissue engineering scaffolds for both hard and soft tissues. Representative tissue types include, but are not limited to, cardiovascular (including blood vessel, artery, and heart valve), cornea and other ocular tissues, pancreas, alimentary tract (e.g., esophagus and intestine), ureter, bladder, skin, cartilage, dental, gingival tissue, bone, liver, kidney, genital organs (including penis, urethra, vagina, uterus, clitoris, and testis), nerve, spinal cord, meniscus, pericardium, muscle (e.g., skeletal), tendon, ligament, trachea, phalanges and small joints, fetal, and breast.

A further advantage of some of the compositions described herein is their ability to be sterilized by radiation sources, in addition to ethylene oxide. Moreover, certain compositions described herein have the additional advantage of good shelf stability, resistance to hydrolysis by water and moisture, and thus less restrictive packaging needs to exclude moisture after preparation, fabrication, and during storage.

Another advantage to using the compositions described herein is the ability to create three dimensional polymer scaffold systems with properties in different regions. This can be achieved by combining the compositions described herein either in different forms, or combining different compositions to make one or more forms. For example, a specific composition may be processed into a fibrous form, and then subsequently processed and combined with another different fibrous or non-fibrous composition. Such combinations may be achieved by weaving, melt processing, solvent processing, coating, and other methods known to those skilled in the art.

Those skilled in the art will recognize, or be able to ascertain using no more than routine experimentation, many equivalents to the specific embodiments of the invention described herein. The references cited herein are hereby incorporated by reference.

Modifications and variations of the present invention will be obvious to those of skill in the art from the foregoing detailed description. Such modifications and variations are intended to come within the scope of the following claims.

I claim:

1. A method for producing a bioabsorbable biocompatible polymer composition comprising:

selecting a tissue structure and measuring one or more mechanical properties selected from the group consisting of stress, strain, stress-strain, stress-strain hysteresis, stress-strain relaxation, viscoelasticity, contraction stress, resting stress, Young's modulus, tensile strength, durability, yield point, failure strength, toughness, ductility, softness, hardness, creep, elastic deformation, wear resistance, shear failure, roughness, compressive strength, load capacity, modulus of elasticity, ultimate compressive strength, yield strength, stress-strain relationship, scratch resistance, abrasion resistance, flexural modulus, shear modulus, contact angle, surface tension, adhesive strength, surface free energy, bending strength, shear strength, bonding strength, bending strength, bending stiffness, compressive modulus, bending modulus, fracture toughness, elongation, fiber strength, fiber modulus, fiber elongation, thermal expansion coefficient, fracture toughness, static and dynamic elasticity, longitudinal stretch, stress, and strain, radial stretch, stress and strain, circumferential stretch, stress and strain, ultimate elongation, viscosity, expansion, static and kinetic coefficients of friction, plasticity, axial tension, shock absorbance, bearing strength, formability, rigidity, stress rupture, bend radius, impact strength, and fatigue strength, equivalent to the same properties of a differentiated tissue or tissue structure, and selecting from a combination of monomers that can be polymerized to make a polymer, one or more inonomers which when linked in a polymeric form, have the mechanical property or properties of the tissue or tissue structure.

2. The method of claim 1 wherein the tissue structure is selected from the group consisting of cardiovascular structures gastrointestinal structures, kidney, genitourinary structures including bladder, ureter, and urethra, musculoskeletal structures including bone, cartilage, tendon, and ligament, nervous system structures, oral tissues, periodontal tissues, and skin tissue.

3. The method of claim 1 wherein the monomers are selected from hydroxy acids.

4. The method of claim 1 wherein the polymer is selected from the group consisting of polyester, poly(orthoester), polyanhydride, polyphosphazene, polyesteramide, polypeptide, polyamide, polydihydropyran, and polycyanoacrylate.

5. The method of claim 1 wherein the polymer contains one or more linkages selected from the group consisting of ester, amide, urethane, carbonate, iminocarbonate, oxalate, oxamate, orthoester, anhydride, phosphazene, glycoside, and ether linkages.

6. The method of claim 2 wherein the cardiovascular structure is selected from the group consisting of heart valves and blood vessels.

* * * * *